(12) United States Patent
Boyer et al.

(10) Patent No.: US 9,440,999 B2
(45) Date of Patent: Sep. 13, 2016

(54) ACTIVATION OF METAL SALTS WITH SILYLHYDRIDES AND THEIR USE IN HYDROSILYLATION REACTIONS

(71) Applicants: Julie L. Boyer, Watervliet, NY (US); Aroop Kumar Roy, Mechanicville, NY (US)

(72) Inventors: Julie L. Boyer, Watervliet, NY (US); Aroop Kumar Roy, Mechanicville, NY (US)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 0 days.

(21) Appl. No.: 14/278,099

(22) Filed: May 15, 2014

(65) Prior Publication Data

US 2014/0343311 A1    Nov. 20, 2014

Related U.S. Application Data

(60) Provisional application No. 61/823,599, filed on May 15, 2013.

(51) Int. Cl.
*C07F 7/18* (2006.01)
*C07F 7/08* (2006.01)
*B01J 31/18* (2006.01)
*B01J 31/22* (2006.01)

(52) U.S. Cl.
CPC .......... *C07F 7/1876* (2013.01); *B01J 31/1815* (2013.01); *B01J 31/2239* (2013.01); *C07F 7/0849* (2013.01); *C07F 7/0879* (2013.01); *C07F 7/0896* (2013.01); *C07F 7/184* (2013.01); *C07F 7/1836* (2013.01); *B01J 2231/323* (2013.01); *B01J 2531/007* (2013.01); *B01J 2531/72* (2013.01); *B01J 2531/821* (2013.01); *B01J 2531/842* (2013.01); *B01J 2531/845* (2013.01); *B01J 2531/847* (2013.01)

(58) Field of Classification Search
CPC .. C07F 7/1876; C07F 7/0896; C07F 7/0849; C07F 7/1836; C07F 7/0879; C07F 7/184; B01J 31/1815; B01J 31/2239
USPC .................................................. 556/479, 485
See application file for complete search history.

(56) References Cited

U.S. PATENT DOCUMENTS

| 3,159,601 | A | 12/1964 | Ashby et al. |
|---|---|---|---|
| 3,220,972 | A | 11/1965 | Lamoreaux |
| 3,296,291 | A | 1/1967 | Chalk et al. |
| 3,775,452 | A | 11/1973 | Karstedt |
| 3,928,629 | A | 12/1975 | Chandra et al. |
| 4,550,152 | A | 10/1985 | Faltynek |
| 4,572,791 | A | 2/1986 | Onopchenko et al. |
| 4,578,497 | A | 3/1986 | Onopchenko et al. |
| 4,729,821 | A | 3/1988 | Timmons et al. |
| 4,788,312 | A | 11/1988 | Paciorek et al. |
| 5,026,893 | A | 6/1991 | Paciorek |
| 5,166,298 | A | 11/1992 | Friedman et al. |
| 5,331,075 | A | 7/1994 | Sumpter et al. |
| 5,432,140 | A | 7/1995 | Sumpter et al. |
| 5,866,663 | A | 2/1999 | Brookhart et al. |
| 5,955,555 | A | 9/1999 | Bennett |
| 6,103,946 | A | 8/2000 | Brookhart et al. |
| 6,214,761 | B1 | 4/2001 | Bennett |
| 6,265,497 | B1 | 7/2001 | Herzig |
| 6,278,011 | B1 | 8/2001 | Chen et al. |
| 6,281,303 | B1 | 8/2001 | Lavoie et al. |
| 6,297,338 | B1 | 10/2001 | Cotts et al. |
| 6,417,305 | B2 | 7/2002 | Bennett |
| 6,423,848 | B2 | 7/2002 | Bennett |
| 6,432,862 | B1 | 8/2002 | Bennett |
| 6,451,939 | B1 | 9/2002 | Britovsek |
| 6,455,660 | B1 | 9/2002 | Clutton et al. |
| 6,458,739 | B1 | 10/2002 | Kimberley et al. |
| 6,458,905 | B1 | 10/2002 | Schmidt et al. |
| 6,461,994 | B1 | 10/2002 | Gibson et al. |
| 6,472,341 | B1 | 10/2002 | Kimberley et al. |
| 6,620,895 | B1 | 9/2003 | Cotts et al. |
| 6,657,026 | B1 | 12/2003 | Kimberley et al. |
| 7,053,020 | B2 | 5/2006 | DeBoer et al. |
| 7,148,304 | B2 | 12/2006 | Kimberley et al. |
| 7,161,005 | B2 | 1/2007 | Schlingloff et al. |
| 7,247,687 | B2 | 7/2007 | Cherkasov et al. |
| 7,268,096 | B2 | 9/2007 | Small et al. |
| 7,429,672 | B2 | 9/2008 | Lewis et al. |
| 7,442,819 | B2 | 10/2008 | Ionkin et al. |
| 7,456,285 | B2 | 11/2008 | Schlingloff et al. |
| 7,696,269 | B2 | 4/2010 | Cruse et al. |
| 8,236,915 | B2 | 8/2012 | Delis et al. |
| 8,415,443 | B2 | 4/2013 | Delis et al. |

(Continued)

FOREIGN PATENT DOCUMENTS

| CN | 1727349 | 2/2006 |
|---|---|---|
| EP | 0786463 | 7/1997 |

(Continued)

OTHER PUBLICATIONS

Shaikh et al., Organic Letters, vol. 9, No. 26, pp. 5429-5432 (2007).*

(Continued)

*Primary Examiner* — Porfirio Nazario Gonzalez

(74) *Attorney, Agent, or Firm* — Joseph E. Waters; McDonald Hopkins LLC

(57) ABSTRACT

The invention relates generally to transition metal salts, more specifically to iron, nickel, cobalt, manganese and ruthenium salts, activated with silylhydrides, and their use as efficient hydrosilylation catalysts.

49 Claims, No Drawings

(56) References Cited

U.S. PATENT DOCUMENTS

| | | |
|---|---|---|
| 2002/0058584 A1 | 5/2002 | Bennett |
| 2006/0263675 A1 | 11/2006 | Adzic et al. |
| 2007/0264189 A1 | 11/2007 | Adzic et al. |
| 2008/0262225 A1 | 10/2008 | Schlingloff et al. |
| 2008/0293878 A1 | 11/2008 | Funk et al. |
| 2009/0068282 A1 | 3/2009 | Schlingloff et al. |
| 2009/0296195 A1 | 12/2009 | Fontana et al. |
| 2011/0009565 A1 | 1/2011 | Delis et al. |
| 2011/0009573 A1 | 1/2011 | Delis et al. |
| 2012/0130021 A1 | 5/2012 | Tondreau et al. |
| 2012/0130105 A1 | 5/2012 | Lewis et al. |
| 2012/0130106 A1* | 5/2012 | Chirik .............. C07F 7/0879 556/467 |
| 2013/0158281 A1 | 6/2013 | Weller et al. |
| 2014/0051822 A1 | 2/2014 | Atienza et al. |
| 2014/0243486 A1 | 8/2014 | Roy et al. |
| 2014/0330024 A1 | 11/2014 | Atienza et al. |
| 2014/0330036 A1 | 11/2014 | Lewis et al. |
| 2014/0343311 A1 | 11/2014 | Boyer et al. |
| 2015/0080536 A1 | 3/2015 | Diao et al. |
| 2015/0137033 A1 | 5/2015 | Diao et al. |

FOREIGN PATENT DOCUMENTS

| | | |
|---|---|---|
| GB | 2013207 | 8/1979 |
| TW | 200902541 | 1/2009 |
| WO | 9210544 | 6/1992 |
| WO | 02088289 | 11/2002 |
| WO | 03042131 | 5/2003 |
| WO | 2008085453 | 7/2008 |
| WO | 2011006044 | 1/2011 |
| WO | 2012/007139 | 1/2012 |
| WO | 2012071359 | 5/2012 |
| WO | 2013/043783 | 3/2013 |
| WO | 2013043846 | 3/2013 |

OTHER PUBLICATIONS

Nashiyama et al., Chemical Communications, pp. 760-762 (2007).*
Kamata et al., Organometallics, vol. 31, pp. 3825-3828 (2012).*
Toma et al., J. Braz. Chem. Soc., vol. 7, No. 6, 391-394, 1996.
Suzuki, et al., "Random and block copolymerizations of norbornene with conjugated 1,3-dienes catalyzed by novel No compounds involving N- or O-donated ligands" Reactive & Functional Polymers 59 (2004) 253-266, May 6, 2004.
Ittel et al., DuPont's Versipol® Late Metal Polymerization Catalysts, http://www.nacatsoc.org/18nam/Orals/044-Ittel-DuPont's%20Versipol%C2%AE%20Late%20Metal%20Polymerization.pdf.
Seki et al., "Single-Operation Synthesis of Vinyl silanes from Alkenes and Hydrosilanes with the Aid of Ru (CO)12," Am. Chem. Soc., J. Org. Chem. 1986, 51, 3890-3895, Osaka, Japan.
Oro et al. "Hydrosilylation of Alkenese by Iridium Complexes," J. Mol. Catalysis, 1986, 37, 151-156.
Naumov et al, "Selective Dehydrogentative Silylation-Hydrogenation Reaction of Divinyldisiloxane with Hydrosilane Catalyzed by an Iron Complex," Journal of the American Chemical Society, 2012, vol. 134, Issue 2, 804-807, Osaka, Japan.
McAtee et al., "Preparation of Allyl and Vinyl Silanes by the Palladium-Catalyzed Silylation of Terminal Olefins: A Silyl-Heck Reaction**," Angewandte Chemie, Int. Ed. 2012, 51, 3663-3667.
Marciniec et al., "Competitve silylation of olefins with vinylsilanes and hydrosilanes photocatalyzed by iron carbonyl complexes," Inorg. Chem. Commun. 2000, 3, 371.
Lu et al, "Iridium-Catalyzed (Z)-Trialkylsilylation ofTerminal Olefins," J. Org. Chem, 2010, 75, 1701-1705, Dallas, Texas.
Kuo, et al., "Electrochemical studies of nickel bis(2,2':6',2''-terpyridine) with alkyl/aryl/allyl bromides and activeated olefins in nonaqueous solvents" Jiemian Kexue Huishi, vol. 15, Issue 1, pp. 23-42, Journal, 1992, Coden: CMKCEW, ISSN: 1026-325X.
Kakiuchi et al., "Dehydrogenative Silylation of 1,5-Dienes with Hydrosilanes Catalyzed by RhCl (PPh3)3," Am. Chem. Soc., Organometallics, 1993, 12, 4748-4750, Kagawa, Japan.
Kakiuchi et al., "Completely Selective Synthesis of (E)-B-(triethylsilyl)styrenes by Fe3(CO)12-catalyzed Reaction of Styrenes With Triethylsilane," Journal of Organometallic Chemistry 1993, 456, 45-47, Osaka, Japan.
Humphries et al., "Investigations into the Mechanism of Activation and Initiation of Ethylene Polymerization by Bis (imino)pyridine Cobalt Catalysts: Synthesis, Structures, and Deuterium Labeling Studies," Organometallics 2005, 24, 2039-2050, London, United Kingdom.
Fernandez et al., "Synthesis and Reactions of Dihydrido(triethylalyl)(1,5-cycloctadiene)-Iridium(III) Complexes: Catalysts for Dehydrogneative Silylation of Alkenese," Organometallics, 1986, 5, 1519-1520.
Chen et al., "General Synthesis of Di-u-oxo Dimanganese Complexes as Functional Models for the Oxygen Evolving Complex of Photosystem II" Inorg. Chem. 2005, 44, 7661-7670.
Bowman et al, "Synthesis and Molecular and Electronic Structures of Reduced Bis(imino) pyridine Cobalt Dinitrogen Complexes: Ligand versus Metal Reduction," J. Am. Chem. Soc., 2010, 132, 1676-1684, Germany.
Anselment et al., "Activation of Late Transition Metal Catalysts for Olefin Polymerizations and Olefin/CO Copolymeriations," Dalton Transactions, vol. 34, pp. 4525-4672.
Atienza, et al., "Olefin hydrosilylation and dehydrogenative silylation with bis(imino) pyridine iron and cobalt catalysts," Abstracts of Papers, 244th ACS National Meeting & Exposition, Philadelphia, PA, Aug. 19-23, 2012.
Atienza, "Reactivity of Bis(Iminio)Pyridine Cobalt Complexes in C-H Bond Activation and Catalytic C-C and C-Si Bond Formation" PhD thesis, Jun. 2013, Princeton University.
Shaikh et al., "Iron-Catalyzed Enantioselevtive Hydrosilylation of Keytones," Angew. Chem. Int. Ed., 2008, 47, 2497-2501.
De Bo et al., "Hydrosilylation of Alkynes Mediated by N-heterocyclic Carben Platinum(0) Complexes," Organometallics, 2006, 25, 1881-1890.
Boudjouk et al., "Exclusive 13-hydrosilylation of acrylates catalysed by copper-tetramethylethylenediamine ," Journal of Organometallic Chemistry, Jan. 1, 1993, pp. 41-43.
Brookhart et al., "Mechanism of a cobalt(III)-catalyzed olefin hydrosilation reaction: direct evidence for a silyl migration pathway," J. Am. Chem. Soc. 1993, 115, 2151.
Castro, Pascel M. et al., "Iron-Based Catalysts Bearing Bis(imido)-Pyridine Ligands for the Polymerization of tert-Butyl Acrylate," Journal of Polymer Science: Part A: Polymer Chemistry, vol. 41, pp. 1380-1389 (2003).
Cornish, et al., "Homogeneous catalysis: VI. Hydrosilylation using tri(pentanedionato)rhodium(III) or tetrakis(μ-acetato) Dirhodium(II) as Catalysts," Journal of Organometallic Chemistry, Elsevier-Sequoia S.A. Lausanne, CH, vol. 172, No. 2, Jun. 12, 1979, pp. 153-163.
Chuit et al. "Reactivity of penta- and hexacoordinate silicon compounds and their role as reaction intermediates," Chem. Rev. 1993, 93, 1371-1448.
De Rycke et al., "Toward reactant encapsulation for substrate-selectivity," Tetrahedron Lett. 2012, 53, 462.
Doucette, "Homogeneous Iron Catalysts With Redox-Active Ligands: Synthesis and Electronic Structure," Dissertation Cornell University, Aug. 2006.
Doyle et al., "Addition/Elimination in the Rhodium(II) Perfluorobutyrate Catalyzed Hydrosilylationo of 1-Alkenes. Rhodium Hydride Promoted Isomerization and Hydrogenation," Organometallics, 1992, 11, 549-555, San Antonio, Texas.
Falck, J. R. et al. "Iridium-Catalyzed (Z)-Trialkylsilylation of Terminal Olefins," J. Org. Chem. 2010, 75, 1701.
Figgins et al., "Complexes of Iron(II), Cobalt(II) and Nickel(II) with Biacetyl-bis-methlylimine, 20Pyridinal-methylimine and 2,6-Pyridindial-bis-methylimine" J. Am. Chem. Soc. 1960, vol. 82, 820-824.
Gandon, et al., "Silicon-Hydrogen Bond Activation and Hydrosilylation of Alkenes Mediated by CpCo Complexes: A Theoretical Study," J. Am. Chem. Soc. 2009, 131, 3007.

(56) References Cited

OTHER PUBLICATIONS

Hori et al., "Ruthenium Complex-Catalyzed Silylation of Olefins. Selective Sysnthesis of Allysilanes," Bull. Chem. Soc. Jpn., 1988, 61, 3011-3013, Kyoto, Japan.
Itoh et al., "Disproportionation reactions of organohydrosilanes in the presence of base catalysts" J. Organomet. Chem., 2001, 629, 1-6.
Ivchenko et al., "A convenient approach for the synthesis of 2,6-diformyl- and 2,6-diacetylpyridines," Tetrahedron Lett. 2013, 54, 217.
Fruchtel et al; "Organic Chemistry on Solid Supports," Angewandte Chemie International Edition in English, 1996, vol. 35, Issue 1, pates 17-42.
Junge et al., "Iron-Catalyzed Reducation of Carboxylic Esters to Alcohols," European Journal of Organic Chemistry, vol. 2013, No. 11, Mar. 1, 2013, pp. 2016-2065.
Knijnenburg et al., "Olefin hydrogenation using diimine pyridine complexes of Co and Rh," Journal of Molecular Catalysis, 232 (2005), No. 1-2, pp. 151-159.
Marciniec, Bogdan, "Catalysis by Transition Metal Complexes of Alkene Silylation—Recent Progress and Mechanistic Implications," Coordination Chemistry Reviews, 249 (2009) 2374-2390.
Marciniec et al. "Encyclopedia of Catalysis" pp. 6,7, and 20, Mar. 5, 2010.
Martinez, Remi et al., "C-C Bond Formation via C-H Bond Activation Using an in Situ-Generated Ruthenium Catalyst," Journal of the American Chemical Society, vol. 131, pp. 7887-7895 (2009).
McAtee et al, "Rational Design of a Second Generation Catalyst for Preparation of Allylsilanes Using the Silyl-Heck Reaction," J. Am. Chem. Soc. 2014, 136 (28), 10166-10172.
Bareille et al., "First Titanium-Catalyzed anti-1,4-Hydrosilylation of Dienes," Organometallics, 2005, 24(24), 5802-5806.
Nishiyama et al., "An Iron-Catalysed Hydrosilylation of Ketones," Chem. Commun., Royal Society of Chemistry, 2007, 160-762.
Furuta et al., "Highly efficient catalytic system for hydrosilylation of ketones with iron(II) acetate—thiophenecarboxylate," Tetrahedron Letters, 2008, vol. 49, Issue 1, pp. 110-113.
Ojima et al., "Regioselective hydrosilylation of 1,3-dienes catalyzed by phosphine complexes of palladium and rhodium," J. Organomet. Chem. 1978, 157, 359-372.
Pettigrew, "Synthetic Lubricants and High Performance Fluids, Ch. 12 Silahydrcarbons" (second edition), L. R. Rudnick and L. R. Shubkin (Editors), Marcel Dekker, NY 1999, pp. 287-296.
Poyatos, Macarena et al., "Coordination Chemistry of a Modular N,C-Chelating Oxazole-Carbene Ligand and Its Applications in Hydrosilylation Catalysis," Organometallics, vol. 25, pp. 2634-2641 (2006).
Reiff, W. M. et al., "Mono(2,2',2"-terpyridine) Complexes of Iron(II)," Journal of Inorganic Chemistry, vol. 8, No. 9, pp. 2019-2021 (1969).
Parker et al. "1,2-Selective Hydrosilylation of Conjugated Dienes," J. Am. Chem. Soc., 2014, 136 (13), pp. 4857-4860.
Woo et al., "Redistribution of Bos- and Tris(silyl)methanes Catalyzed by Red-Al," Bull. Korean. Chem. Soc. 1996, 17, 123-125.
Wu et al., "A Strategy for the Synthesis of Well-Defined Iron Catalysts and Application to Regioselective Diene Hydrosilylation," Journal of the American Chemical Society, vol. 132, No. 38. Sep. 29, 2010, pp. 13214-13216.
Yi, Chae S. et al., "Regioselective Intermolecular Coupling Reaction of Arylketones and Alkenes Involving C-H Bond Activation Catalyzed by an in Situ Formed Cationic Ruthenium Hydride Complex," Organometallics, vol. 28, pp. 4266-4268 (2009).
Zhang et al., "Ferrous and Cobaltous Chlorides Bearing 2,8-Bis(imino)quinolines: Highly Active Catalysts for Ethylene Polymerization at High Temperature," Organometallics, vol. 29, pp. 1168-1173 (2010).
Benkeser et al., "Chloroplatinic acid catalyzed additions of silanes to isoprene," J. Organomet. Chem. 1978, 156, 235-244.
Schmidt, Roland et al., "Heterogenized Iron(II) Complexes as Highly Active Ethene Polymerization Catalysts," Journal of Molecular Catalysis A: Chemical, vol. 179, pp. 155-173 (2002).
Shaikh et al., "A Convenient and General Iron-Catalyzed Hydrosilylation of Aldehydes," Organic Letters, vol. 9, No. 26, Dec. 1, 2007, pp. 5429-5432.
Small, B. L., et al. "Highly Active Iron and Cobalt Catalysts for the Polymerization of Ethylene," J. Am. Chem. Soc. 1998, 120(16), 4049-4050.
International Preliminary Report on Patentability of PCT/US2014/038082 mailed May 15, 2015.
International Search Report and Written Opinion of the International Searching Authority for PCT/US2014/038082 mailed Aug. 11, 2014.
Archer et al., "Arene Coordination in Bis(imino)pyridine Iron Complexes: Identification of Catalyst Deactivation Pathways in Iron-Catalyzed Hydrogenation and Hydrosilation," Organometallics, vol. 25, pp. 4269-4278 (2006).
Bowman et al., "Reduced N-Alkyl Substituted Bis(imino)pyridine Cobalt Complexes: Molecular and Electronic Structures for Compounds Varying by Three Oxidation States," Inorg. Chem. 2010, 49, 6110-6123, Germany.
Zhu et al., 2"A Measure for *-Donor and *-Acceptor Properties of Diiminepyridine-Type Ligands," Organometallics 2008, 27, 2699-2705.
Zhu et al., "(Py)2Co(CH2SiMe3)2 As an Easily Accessible Source of "CoR2"," Organometallics, 2010, 29 (8), 1897-1908.
Yeung, et al., "Cobalt and iron complexes of chiral C1- and C2-terpyridines: Synthesis, characterizationa dn use in catalytic asymmetric cyclopropanation of styrenes." Inorganica Chimica Acta 362 (2009) 3267-3273.
Bart et al., "Electronic Structure of Bis(imino)pyridine Iron Dichloride, Monochloride, and Neutral Ligand Complexes: A Combined Structural, Spectroscopic, and Computational Study," J. Am. Chem. Soc. 2006, 128, 13901-13912.
Bart et al., "Preparation and Molecular and Electronic Structures of Iron(0) Dinitrogen and Silane Complexes and Their Application to Catalytic Hydrogenation and Hydrosilation," Journal of the American Chemical Society, vol. 126, pp. 13794-13807 (2004).
Connelly et al., "Chemical Redox Agents for Organometallic Chemistry," Chem. Rev. 1996, 96, 877-910.
Atienza et al. "Synthesis, Electronic Structure, and Ethylene Polymerization Activity of Bis(imino)pyridine Cobalt Alkyl Cations," Agnewandte Chem. Int. Ed. 2011, 50, 8143-8147.
Glatz et al., "Terpyridine-Based Silica Supports Prepared by Ring-Opening Metathesis Polymerization for the Selective Extraction of Noble Metals," Journal of Chromatography A, vol. 1015, pp. 65-71 (2003).
Nagashima et al., "Dehydrogenative Silylation of Ketones with a Bifunctional Organosilane by Rhodium- Pybox Catalysts," Chem. Soc. of Jpn., Chemistry Letters, 1993, 347-350, Toyohashi, Aichi 441.
Hosokawa et al., "A Chiral Iron Complex Containing a Bis(oxazolinyl)phenyl Ligand: Preparation and Asymmetric Hydrosilylation of Ketones," Organometallics, 29, 5773-5775 (2010).
Kaul et al., "Immobilization of Bis(imino)pyridyliron (II) complexes on Silica," Organometallics, 2002, 21(1), 74-83.
Kim et al., "2,2':6',2"-Terpyridine and Bis(2,2':6',2"-terpyridine)Ruthenium(II) Complex on the Dendritic Periphery," Journal of Organometallic Chemistry, vol. 673, pp. 77-83 (2003).
Kroll et al., "Access to Heterogeneous Atom-Transfer Radical Polymerization (ATRP) Catalysts Based on Dipyridylamine and Terpyridine via Ring-Opening Metathesis Polymerization (ROMP)," Macromolecular Chemistry and Physics, vol. 202, pp. 645-653 (2001).
Field et al., "One-Pot Tandem Hydroamination/Hydrosilation Catalyzed by Cationic Iridium(I) Complexes," Organometallics, vol. 22, pp. 4393-4395, Sep. 25, 2003.
Dekamin et al., "Organocatalytic, rapid and facile cyclotrimerization of isocyanates using tetrabutylammonium phthalimide-N-oxyl and tetraethylammonium 2-(carbamoyl) benzoate under solvent-free conditions," Catalysis communications 12 (2010) 226-230.

(56) References Cited

OTHER PUBLICATIONS

Nesmeyanov et al., "Addition, Substitution, and Telomerization Reactions of Olefins in the Presence of Metal Carbonyls or Colloidal Iron," Tetrahedron, vol. 17, pp. 61-68 (1962).
Pal, et al., "Preparation and hydrosilylation activity of a molybdenum carbonyl complex that features a pentadentate bis (amino)pyridine lignad," Inorg Chem. Sep. 2, 2014; 53(17):9357-65. doi: 10.1021/ic501465v. Epub Aug. 20, 2014.
Jairam et al., "Ester Hydrolysis with 2,6-di(pyrazol-3-yl)pyridines and their Co 11 Complexes in Homogeneous and Micellar Media," Journal of Inorganic Biochemistry 84, 2001, 113-118, Toronto, Ontario, Canada.
Buschbeck et al., "Triethylene Glycol Ether End-grafted Carbosilane Dendrimers: Synthesis and Complexation Behavior," Inorganic Chemistry Communications, vol. 7, pp. 1213-1216, Oct. 13, 2004.
Seckin, "Preparation and Catalytic Properties of a Ru(II) Coordinated Polyimide Supported by a Ligand Containing Terpyridine Units," Journal of Inorganic and Organometallic Polymers and Materials, Apr. 9, 2009, 19(2), 143-151.
Sieh et al., "Metal-Ligand Electron Transfer in 4d and 5d Group 9 Transition Metal Complexes with Pyridine, Diimine Ligands," Eur. J. Inorg. Chem., 2012:444-462. doi 10.1002/ejic.201101072.
Speier et al., "The Addition of Silicon Hydrides to Olefinic Double Bonds. Part II. The Use of Group VIII Metal Catalysts," Journal of the American Chemical Society, vol. 79, pp. 974-979 (1956).
Thammavongsy et al., Ligand-Based Reduction of CO2 and Release of CO and Iron(II). Inorg. Chem., 2012, 51 (17), pp. 9168-9170. DOI: 10:1021/ic3015404. Publication Date (Web): Aug. 20, 2012.
Timpa, "Non-Innocent Pyridine Based Pincer Ligands and Their Role Catalysis" Nov. 1, 2010.
Tondreau, et al., "Enantiopure Pyridine Bis(oxazoline) "Pybox" and Bis(oxazoline) "Box" iron Dialkyl Complexes: comparison to Bis(imino)pyridine Compounds and Application to Catalytic Hydrosilylation of Ketones," Drganometallics, Jun. 9, 2009, 28(13), 3928-3940.
Tondreau, et al "Synthesis and electronic structure of cationic, neutral, and anionic bis (imino)pyridine iron alkyl aomplexes: evaluation of redox activity in single-component ethylene polymerization catalysts." J Am Chem Soc. Oct. 27, 2010; 132(42): 15046-59. doi: 10.1021/ja106575b.
Gibson et al., "The nature of the active species in bis(imino)pyridyl cobalt ethylene polymerisation catalysts," Chem. Commun., 2001, 2252-2253.
Wile, et al. "Reduction chemistry of aryl- and alkyl-substituted bis(imino)pyridine iron dihalide compounds: molecular and electronic structures of [(PDI)2Fe] derivatives." Inorg Chem May 4, 2009; 48(9):4190-200.
Tondreau, et al., "Iron Catalysts for Selective Anti-Markovnikov Alkene Hydrosilylation Using Tertiary Silanes," Science, vol. 335, No. 6068, Feb. 2, 2012. Pp. 567-570.
Abu-Surrah et al., "New bis(imino)pyridine-iron(II)- and cobalt(II)- based catalysts: synthesis, characterization and activity towards polymerization of ethylene" Journal of Organometallic Chemistry 648 (2002) 55-61.
Albon et al., "Metal Carbonyl Complexes Involving 2,6Bix[I-(phenylimino)ethyl]pyridine; Bidentate Corrdination of a Potentially Tridentate Ligand" Inorganica Chimica Acta, 159 (1989) 19-22.
Alyea et al., "Terdentate NNN Donor Ligands Derived from 2,6-Diacetylpyridine" Syn. React. Inorg. Metal-Org. Chem., 1(6), 535-544 (1974).
Bouwkamp, "Iron-Catalyzed [2π+2π] Cycloaddition of α, ω-Dienes the Importance of Redoxactive Supporting Ligands" Journal of the American Chemical Society, 2006, V128 N41, pp. 13340-13341.
Biritovsek et al., "Novel Olefin Polymerization Catalysts Based on Iron and Cobalt," Chem. Commun., 1998, 849-850.
Cetinkaya et al., "Ruthenium(ii) complexes with 2,6-pyridyl-diimine ligands: synthesis, characterization and catalytic activity in epoxidation reactions" Journal of Molecular Catalysis A: Chemical 142 (1999) 101-112.
Corey et al., "Reactions of Hydrosilanes with Transition-Metal Complexes: Formation of Stable Transition-Metal Silyl Compounds," Journal of Chemical Reviews, vol. 99, pp. 175-292 (1999).
Haarman et al., "Reactions of [RhCI(diene)]2 with Bi- and Terdentate Nitrogen Ligands. X-ray Structures of FiveCoordinate Complexes," Am. Chem. Soc., Organometallics 1997, 16, 54-67.
Kickelbick et al., New J. Chem., 2002, 26, 462-468.
Kooistra et al., Inorganica Chimica Acta 357 (2004) 2945-2952.
Lapointe, et al., "Mechanistic Studies of Palladium(II)-Catalyzed Hydrosiliation and Dehydrogenative Silation Reactions," J. Amer. Chem. Soc. 119 (1997), pp. 906-917.
Lewis et al., "Hydrosilylation Catalyzed by Metal Colloids: A Relative Activity Study," Organometallics, 9 (1990), 321-625.
Lions et al., J. Chem. Soc. (A) 1957, vol. 79, 2733-2738.
Lu et al., "The Molecular Structure of a Complex of a 2,6-Diimino-Pyridine as a Bidentate Liandd with Molybdenum Carbonyl" Inorganica Chimica Acta, 134 (1987) 229-232.
Pangborn et al., "Safe and Convenient Procedure for Solvent Purification," Oraganometallics, 15:1518 (1996).
Randolph, Claudia L et al., "Photochemical Reactions of (η5-Pentamethylcyclopentadienyl)dicarbonyliron-Alkyl and Silyl Complexes: Reversible Ethylene Insertion into an Iron-Silicon Bond and Implications for the Mechanism of Transition-Metal-Catalyzed Hydrosilation of Alkenes," Journal of the American Chemical Society, vol. 108, pp. 3366-3374 (1986).
Russell et al., "Synthesis of Aryl-Substituted Bis(imino)pyridine Iron Dinitrogen Complexes," Inorg. Chem. 2010, 49, 2782-2792.
Sacconi et al., "High-spin Five-Co-Ordinate Nickel (II) and Cobald (II) Complexes with 2,6-Diacetylepyridinebis (imines)," J. Chem. Soc. (A), 1968, 1510-1515.
Tondreau et al., "Bis(imino)pyridine Iron Complexes for Aldehyde and Ketone Hydrosilylation," Am. Chem. Soc., 2008, vol. 10, No. 13, 2789-2792.

* cited by examiner

ACTIVATION OF METAL SALTS WITH SILYLHYDRIDES AND THEIR USE IN HYDROSILYLATION REACTIONS

CROSS-REFERENCE TO RELATED APPLICATIONS

This application claims the benefit of U.S. Provisional Application Ser. No. 61/823,599 filed May 15, 2013, which is incorporated by reference herein in its entirety.

FIELD OF INVENTION

The invention relates generally to transition metal salts, more specifically to iron, nickel, cobalt, manganese, and ruthenium salts, activated with silylhydrides, and their use as efficient hydrosilylation catalysts.

BACKGROUND OF THE INVENTION

Hydrosilylation chemistry, involving the reaction between a silylhydride and an unsaturated organic group, is the basis for synthetic routes to produce commercial silicone products such as silicone surfactants, silicone fluids and silanes as well as many addition cured products including sealants, adhesives, and silicone-based coatings. Conventionally, hydrosilylation reactions have been typically catalyzed by precious metal catalysts, such as platinum or rhodium metal complexes.

Various precious metal complex catalysts are known in the art. For example, U.S. Pat. No. 3,775,452 discloses a platinum complex containing unsaturated siloxanes as ligands. This type of catalyst is known as Karstedt's catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

Although these precious metal compounds and complexes are widely accepted as catalysts for hydrosilylation reactions, they have several distinct disadvantages. One disadvantage is that the precious metal complex catalysts are inefficient in catalyzing certain reactions. For example, in the case of hydrosilylations of allyl polyethers with silicone hydrides using precious metal complex catalysts, use of a large excess of allyl polyether, relative to the amount of silicone hydride, is needed to compensate for the lack of efficiency of the catalyst in order to ensure complete conversion of the silicone hydride to a useful product. When the hydrosilylation reaction is completed, this excess allyl polyether must either be: (A) removed by an additional step, which is not cost-effective, or (B) left in the product which can result in reduced performance of this product in end-use applications. Additionally, allyl polyether hydrosilylation with conventional precious metal catalysts typically results in a significant amount of undesired side products such as olefin isomers, which in turn can lead to the formation of undesirably odoriferous byproduct compounds.

Further, due to the high price of precious metals, catalysts derived from these metals can constitute a significant proportion of the cost of silicone formulations. Over the last two decades, global demand for precious metals, including platinum, has sharply increased, driving prices several hundred folds higher, thereby precipitating the need for effective, low cost replacement catalysts.

As an alternative to precious metals, certain iron complexes have been disclosed as suitable for use as ketone and/or aldehyde hydrosilylation catalysts. Illustratively, technical journal articles have disclosed that iron salts treated with phosphine or nitrogen compounds catalyze the hydrosilylation reaction of activated double bonds such as aldehydes and ketones at long reaction times. (Beller et al. Organic Letters, 2007, 26, 5429-5432; Beller et al. Angew. Chem. Int. Ed., 2008, 47, 2497-2501; Nishiyama et al. Tetrahedron Letters, 2008, 49, 110-113) Nishiyama (Chem. Commun. 2007, 760-762) reported the poor activity of iron acetate and $2,6\text{-}(2,4,6\text{-}Me_3\text{-}C_6H_2N=CMe)_2 C_5H_3N$ ($^{Mes}$PDI) in the hydrosilylation of methyl(4-phenyl)phenylketone (7% after 20 h at 65° C.).

Certain iron complexes have also been disclosed as suitable for use as alkene hydrosilylation catalysts. For example, $Fe(CO)_5$ has been shown to catalyze hydrosilylation reactions at high temperatures: Nesmeyanov, A. N. et al., Tetrahedron 1962, 17, 61; Corey, J. Y et al., J. Chem. Rev. 1999, 99, 175; C. Randolph, M. S. Wrighton, J. Am. Chem. Soc. 1986, 108, 3366). However, undesirable by-products such as unsaturated silyl-olefins, resulting from dehydrogenative silylation, were formed as well.

A five-coordinate Fe(II) complex containing a pyridine di-imine (PDI) ligand with isopropyl substituents at the ortho positions of the aniline rings has been used to hydrosilylate an unsaturated hydrocarbon (1-hexene) with primary and secondary silanes such as $PhSiH_3$ or $Ph_2SiH_2$ (Bart et al., J. Am. Chem. Soc., 2004, 126, 13794; Archer, A. M. et al. Organometallics 2006, 25, 4269). However, one limitation of these catalysts is that they are only effective with the aforementioned primary and secondary phenyl-substituted silanes, and not with, for example, tertiary or alkyl-substituted silanes such as $Et_3SiH$, or with alkoxy substituted silanes such as $(EtO)_3SiH$.

Recently, new and inexpensive Fe, Ni, Co and Mn complexes containing a terdentate nitrogen ligand have been found to selectively catalyze hydrosilylation reactions, as described in co-pending U.S. Pat. Nos. 8,236,915 and 8,415,443. Chirik has reported the formation of the catalytically inactive $Fe(PDI)_2$ species. The undesired $Fe(PDI)_2$ is formed by treatment of $PDIFeBr_2$ with the reductant Na(Hg). The yield of the $Fe(PDI)_2$ species increases when the reduction is performed in the presence of excess free PDI. (Chirik et al. Inorg. Chem. 2010, 49, 2782-2792. Chirik et al. Inorg. Chem. 2009, 48, 4190-4200).

One restriction of these new non-precious metal based catalysts, however, is that they are normally extremely sensitive to air and moisture, and thus are unlikely to perform well or consistently if exposed to air or moisture prior to their use. For this reason, these catalysts are typically prepared and stored under hermetically inert conditions such as in a dry box. Since it is impractical to install and use such highly inert-atmosphere equipment widely on an industrial scale, the use of these catalysts in a commercial setting may be economically prohibitive. Accordingly, there is a need in the industry for non-precious metal-based catalysts that do not require manufacturing and storing under inert conditions.

Methods are known in the art to activate catalyst precursors in-situ. The most well-known example is the activation of Ziegler-Natta catalyst by methylaluminoxane (MAO) for the production of polypropylene from propene (Y. V. Kissin Alkene Polymerization Reactions with Transition Metal Catalysts, Elsevier, 2008, Chapter 4).

Additional examples of catalyst activation are also known. U.S. Pat. No. 5,955,555 discloses the activation of certain iron or cobalt PDI dianion complexes by polymethylaluminoxane (PMAO) for olefin polymerization. U.S. Pat. No. 4,729,821 discloses the in-situ activation of Ni-catalysts by applied electrical potentials for the hydrogenolysis of ethane and ethylene. Martinez et al. demonstrated the in-situ activation of a [RuCl$_2$(p-cym)]$_2$ complex by phosphine ligands in a C—C bond formation reaction via C—H bond activation of aryl-compounds (J. Am. Chem. Soc, 2009, 131, 7887). Yi et al. described the in-situ formation of cationic ruthenium hydride complexes which catalyze the regioselective intermolecular coupling reaction of arylketones and alkenes involving C—H bond activation (Organometallics, 2009, 28, 426). More recently, Thomas et al. have described the activation of base metal complexes with ethyl magnesium bromide (Adv. Synth. Catal. 2014, 356(2-3), 584-590).

The in-situ activation of non-precious metal-based catalysts for alkene hydrosilylation reactions has been described. (See, U.S. Patent Application Publication 2012/013106A1). However, this activation employs NaBEt$_3$H, which is sensitive to air and incompatible with alkoxysilanes. Alkoxysilanes are known to undergo dangerous disproportionation reactions with strong hydride donors such as alkali borohydrides or alkali hydrides. (Woo, H.; Song, S.; Cho, E.; Jung, I.; *Bull. Korean Chem. Soc.* 1996, 17, 123-125. Itoh, M.; Ihoue, K.; Ishikawa, J.; Iwata, K. *J. Organomet. Chem.*, 2001, 629 1-6.)

There is a continuing need in the hydrosilylation industry for methods of activating non-precious metal catalysts using milder reducing reagents that are also compatible with alkoxysilanes. The present invention provides one solution toward that need.

SUMMARY OF THE INVENTION

In one aspect, the present invention provides a process for the hydrosilylation of an unsaturated compound in the presence of a metal complex via the activation of the metal complex with a silylhydride and a promoter compound.

In one aspect, the present invention provides a process for the hydrosilylation of an unsaturated compound comprising at least one unsaturated group with a silylhydride in the presence of a metal complex of Formula (I), Formula (II), or a combination thereof:

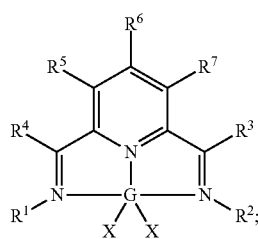

Formula (I)

GXn Formula (II);

wherein the process comprises activating the metal complex with a silylhydride and a promoter compound, and G is Mn, Fe, Ni, Ru, or Co; each occurrence of R$^1$, R$^2$, R$^3$, R$^4$, R$^5$, R$^6$, R$^7$, is independently H, C1-18 alkyl, C1-C18 substituted alkyl, aryl, substituted aryl, or an inert group, wherein any two neighboring R$^1$, R$^2$, R$^3$, R$^4$, R$^5$, R$^6$, and R$^7$ groups taken together may form a ring being a substituted or unsubstituted, saturated, or unsaturated cyclic structure, wherein R$^1$-R$^7$ other than hydrogen, optionally contain at least one heteroatom; X in Formula (I) is an anion; X in Formula (II) is an anion or an oxygen atom, and n=1-3 including non-integers. In another aspect, the present invention provides a process for the hydrosilylation of a composition containing a silylhydride and a compound containing at least one unsaturated group, the process comprising:

reacting a substrate silylhydride with a compound containing at least one unsaturated group in the presence of an activating silylhydride, a promoter compound, and a metal complex to produce a hydrosilylation product containing said complex and/or derivatives thereof, wherein the metal complex is chosen from a complex of Formula (I), Formula (II), or a combination thereof; where Formula (I) is:

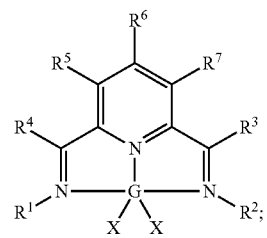

Formula (I)

Formula (II) is: GXn; G is Mn, Fe, Ni, Ru, or Co; each occurrence of R$^1$, R$^2$, R$^3$, R$^4$, R$^5$, R$^6$, R$^7$, is independently H, C1-18 alkyl, C1-C18 substituted alkyl, aryl, substituted aryl, or an inert group, wherein any two neighboring R$^1$, R$^2$, R$^3$, R$^4$, R$^5$, R$^6$, and R$^7$ groups taken together may form a ring being a substituted or unsubstituted, saturated, or unsaturated cyclic structure, wherein R$^1$-R$^7$ other than hydrogen, optionally contain at least one heteroatom; X in Formula (I) is an anion; X in Formula (II) is an anion or an oxygen atom, and n=1-3 including non-integers.

In still another aspect, the present invention is directed to a process for the hydrosilylation of a composition containing a silylhydride and a compound containing at least one unsaturated group, the process comprising: (i) providing a mixture comprising a silylhydride, a compound containing at least one unsaturated group, and a complex according to Formula (I); (ii) contacting said mixture with an activating silylhydride and a promoter compound, optionally in the presence of a solvent, to cause the substrate silylhydride to react with the compound containing at least one unsaturated group to produce a hydrosilylation product containing said complex and/or derivatives thereof, and (iii) optionally removing the complex and/or derivatives thereof from the hydrosilylation product, wherein Formula (I) is:

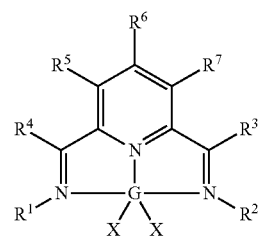

Formula (I)

wherein G is Mn, Fe, Ni, Ru, or Co; each occurrence of R$^1$, R$^2$, R$^3$, R$^4$, R$^5$, R$^6$, R$^7$, is independently H, C1-18 alkyl, C1-C18 substituted alkyl, aryl, substituted aryl, or an inert group, wherein any two of R$^1$, R$^2$, R$^3$, R$^4$, R$^5$, R$^6$, R$^7$ taken together may form a ring being a substituted or unsubstituted, saturated, or unsaturated cyclic structure, wherein R¹-R⁷ other than hydrogen, optionally contain at least one heteroatom.

In yet another aspect, the present invention is directed to a process for the hydrosilylation of a composition containing a silylhydride and a compound containing at least one unsaturated group, the process comprising: (i) providing a mixture comprising a silylhydride, a compound containing at least one unsaturated group, and a complex according to Formula (II); (ii) contacting said mixture with an activating silylhydride and a promoter compound, optionally in the presence of a solvent, to cause the substrate silylhydride to react with the compound containing at least one unsaturated group to produce a hydrosilylation product containing said complex and/or derivatives thereof, and (iii) optionally removing the complex and/or derivatives thereof from the hydrosilylation product, wherein Formula (II) is GXn, where G is Fe, Ru, Ni, Mn, or Co; X is an anion or an oxygen atom, and n=1-3 including non-integers.

DETAILED DESCRIPTION OF THE INVENTION

It has now been surprisingly found that various metal salts and metal compounds can be activated in-situ by a silylhydride to generate effective catalysts for the hydrosilylation of an unsaturated hydrocarbon with the same or different silylhydride or a siloxyhydride. The in-situ activation permits a user to control exactly when the reaction occurs, dramatically facilitates the activation process, and utilizes a significantly milder activating agent. This level of control can aid in the commercial production of materials made by the process, as well as downstream use of the products in applications.

As used herein, "in-situ" is intended to include, but is not limited to, the following situations: (1) the metal based complex, salt or compound of Formula (I) and (II) activated by contacting the metal-based precursor and promoter with a silylhydride when the precursor is present in the reaction mixture of the unsaturated compound and the silylhydride; and (2) the metal based complex, salt or compound of Formula (I) and (II) activated by contacting the metal precursor and promoter with the activating silylhydride to provide an admixture shortly before the admixture contacts the substrate silylhydride and the unsaturated compound. By "shortly before" is meant a time period of less than 24 hours, preferably less than 2 hours, more preferably, less than 30 minutes depending upon the properties of the particular catalyst precursor and the activating silylhydride and promoter used.

As used herein, an "activating silylhydride" is an organosilane or alkoxysilane with at least one SiH unit that, especially in the presence of the promoter, causes a metal salt, compound or complex, to catalyze a hydrosilylation reaction. The efficacy of an activating silylhydride can be determined through experimentation by those skilled in the art.

As used herein, by "unsaturated" is meant one or more double or triple bonds. In a preferred embodiment, it refers to carbon-carbon double or triple bonds.

The process comprises reacting a substrate silylhydride and a compound containing at least one unsaturated group in the presence of an activating silylhydride, a promoter compound, and a metal complex to form a hydrosilylation product comprising the complex and/or derivatives thereof.

The metal complex is chosen from a complex of Formula (I), Formula (II), or a combination of two or more thereof:

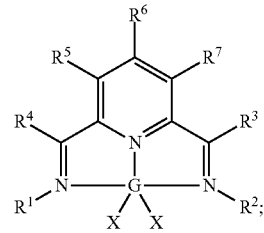

Formula (I)

GXn.

Formula (II)

In Formulas (I) and (II), G is Mn, Fe, Ni, Ru, or Co in any of their respective valence states. Each occurrence of R¹, R², R³, R⁴, R⁵, R⁶, R⁷ is independently chosen from H, C1-18 alkyl, C1-C18 substituted alkyl, aryl, substituted aryl, or an inert group, wherein any two neighboring R¹, R², R³, R⁴, R⁵, R⁶, and R⁷ groups taken together may form a ring being a substituted or unsubstituted, saturated, or unsaturated cyclic structure, wherein R¹-R⁷ other than hydrogen, optionally contain at least one heteroatom.

In Formula (I), X is an anion. In Formula (II), X is an anion or an oxygen atom, and n=1-3 including non-integer numbers. Where X represents an oxygen atom, $GX_n$ may represent an oxide or mixed oxide of the metal G. It will be further understood that the formula of the metal oxide or mixed oxide will vary based on the nature of the metal and the oxidation state(s). For example, iron oxides may be represented variously as FeO, $Fe_2O_3$, or $Fe_3O_4$ ($FeO.Fe_2O_3$). In one embodiment, G is Fe, such as Fe (II) or Fe (III). In one embodiment, X in Formula (I) or (II) is an anion, such as a halogen (F⁻, Cl⁻, Br⁻, I⁻), chelating oxygen containing ligand such an enolate, acetylacetonate, $CF_3R^8SO_3^-$ or $R^9COO^-$, wherein R⁸ is a covalent bond or a C1-C6 alkylene group optionally containing one or more heteroatoms, and R⁹ is a C1-C20 substituted or unsubstituted hydrocarbyl group optionally containing one or more heteroatoms. In one embodiment, X is $R^9COO^-$.

The manner or order in which the respective components for carrying out the process are added to one another is not particularly limited and can be chosen as desired. In one embodiment, the substrate silylhydride, compound containing at least one unsaturated group, activating silylhydride, promoter, and metal complex/salt can be added together in one solution and then reacted. In another embodiment, the process comprises providing a first mixture comprising the metal complex/salt, promoter, and activating silylhydride, and adding a solution of the substrate silylhydride and unsaturated compound to the first mixture. In still another embodiment, the process comprises providing a first mixture of the metal salt, promoter, activating silylhydride, and substrate silylhydride, and subsequently adding the unsaturated compound to the first mixture. In still another embodiment, the process comprises providing a first mixture of the metal salt, promoter, activating silylhydride, and unsaturated compound, and subsequently adding the substrate silylhydride to the first mixture. It will be appreciated that the first mixtures in the above embodiments may be heated or preliminarily reacted prior to addition of the remaining components.

In a further embodiment, the process may comprise providing a first mixture comprising the metal complex/salt, promoter, and activating silane and heating the first mixture; adding the unsaturated compound to the first mixture to form a second mixture, and subsequently adding the substrate silylhydride to the second mixture. In still another further embodiment, the process may comprise providing a first mixture comprising the metal complex/salt, promoter, and activating silylhydride and heating the first mixture; adding the substrate silylhydride to the first mixture to form a second mixture, and subsequently adding the unsaturated compound to the second mixture.

As indicated above, in one embodiment, the present invention is directed to a process for the hydrosilylation of a composition containing a silylhydride and a compound containing at least one unsaturated group, the process comprising: (i) providing a mixture comprising a silylhydride, a compound containing at least one unsaturated group, and a complex according to Formula (I) and/or Formula (II); (ii) contacting said mixture with an activating silylhydride and a promoter compound, optionally in the presence of a solvent, to cause the substrate silylhydride to react with the compound containing at least one unsaturated group to produce a hydrosilylation product containing said complex and/or derivatives thereof, and (iii) optionally removing the complex and/or derivatives thereof from the hydrosilylation product.

It will also be appreciated that, as previously described, the silylhydride employed to activate the metal complex can be the same silylhydride that will react with the unsaturated compound. In such circumstances, the substrate silylhydride and the activating silylhydride can be the same compound, and a single compound can be employed in the process. That is, when the substrate silylhydride is also the activating silylhydride, it is not necessary to utilize separate additions of that material at separate steps in the process.

Non-limiting examples of embodiments of possible hydrosilylation reactions in accordance with the present process are shown schematically in Equation 1:

Equation 1

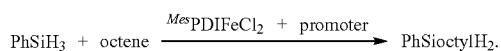

Equation 2

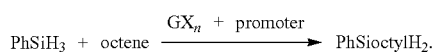

In the embodiments illustrated in Equations 1 and 2, PhSiH$_3$ functions as both the substrate silylhydride and the activating silylhydride.

The methods to prepare the catalyst precursors of the present invention are known to a person skilled in the field. The complex of Formula (I) can be prepared by reacting a PDI ligand with a metal halide, such as FeBr$_2$. Typically, the PDI ligands are produced through condensation of an appropriate amine or aniline with 2,6-diacetylpyridine and its derivatives. If desired, the PDI ligands can be further modified by known aromatic substitution chemistry. An exemplary method to prepare the complex of Formula (I) can be found in *Organometallics* (2010), 29(5), 1168-1173 to Zhang et al.

A wide variety of promoters can be employed in the catalyst activation step. Though not wishing to be bound by any theory or mechanism, the promoter will have a high affinity for coordination to a silicon hydride compound and is able to promote the in-situ formation of a hypercoordinate silicon species. (See, Corriu et al. Chem. Rev., 1993, 93, 1371-1448). Promoters useful in the method of the invention include neutral or ionic compounds selected from the groups consisting of amines, imines, carboxylates, ethers, alcohols, ketones, heterocyclics, and other N and/or O-containing species, or mixtures of two or more thereof. These species may be mono-dentate or multi-dentate. Specific examples of promoters include, but are not limited to, 2,6-pyridine(di) imine type compounds such as, for example, (2,4,6,-Me$_3$C$_6$H$_2$N=CMe)$_2$C$_5$H$_3$N ($^{Mes}$PDI), tetramethylethylenediamine (TMEDA), triethanolamine, lithium acetylacetonate (Liacac), sodium acetate (NaOAc), tetrabutylammonium fluoride (TBAF), o-aminophenol, diacetylpyridine, dimethanolpyridine, phosphines, pinacol, and imidazole. Preferably, the promoter is compatible and does not react with the substrates for the hydrosilylation reaction. In particular, it is desired that the promoter does not catalyze the disproportionation of alkoxysilanes. The promoter $^{Mes}$PDI, for example, does not disproportionate alkoxysilanes such as triethoxysilane.

The reaction components can optionally be disposed in a solvent. The solvent is not limited and can be either polar or non-polar. Any solvent can be used in the method of the invention, as long as it facilitates the activation and the reaction, without deleterious effects. It is not necessary that the complex of Formula (I) or the salt of Formula (II) be dissolved in any mixture to which it is added (e.g., to a mixture of solvent, substrate, promoter mixture, etc.) before the addition of the other components to that mixture.

The metal species of Formulae (I) and (II) can be activated in-situ to generate reactive catalysts effective at selectively catalyzing industrially practiced hydrosilylation reactions. Accordingly, the catalyst precursors of the invention have utility in the preparation of useful silicone products, including, but not limited to, coatings such as release coatings, room temperature vulcanizates, sealants, adhesives, products for agricultural and personal care applications, silicone surfactants for stabilizing polyurethane foams and silyl- or silicone-modified organic polymers.

When used as catalyst precursors for the hydrosilylation reaction, the complexes of Formula (I) can be supported or immobilized on a support material, for example, carbon, silica, alumina, MgCl$_2$ or zirconia, or on a polymer or prepolymer, for example polyethylene, polypropylene, polystyrene, or poly(aminostyrene). The metal complexes can also be supported on dendrimers.

In some embodiments, for the purposes of attaching the catalyst precursors of the invention to a support, it is desirable that at least one of R$^1$ to R$^7$ of the metal complexes, has a functional group that is effective to covalently bond to the support. Exemplary functional groups include but are not limited to SH, COOH, NH$_2$, or OH groups.

In certain embodiments, silica supported catalyst precursors may be prepared via Ring-Opening Metathesis Polymerization (ROMP) technology as discussed in the literature, for example Macromol. Chem. Phys. 2001, 202, No. 5, pages 645-653; Journal of Chromatography A, 1025 (2003) 65-71. In some embodiments, the catalyst precursors can be immobilized on the surface of dendrimers by the reaction of Si—Cl bonded parent dendrimers and functionalized PDI in the presence of a base is as illustrated by Kim et al. in Journal of Organometallic Chemistry 673 (2003) 77-83.

The temperature range for the process of the hydrosilylation is from −50° C. to 250° C., preferably from −10° C. to 150° C. The silylhydride and the compound having at least one unsaturated group are typically mixed in a molar ratio ranging from about 0.5:2 to about 1:0.8, preferably from about 0.8:1.3 to about 1:0.9, and most preferably in a molar ratio of 1:1 of the reactive groups. The molar ratio of the activating silylhydride with respect to the catalyst precursor is between about 1000:1 and 1:1, preferably between about 100:1 and 10:1. The molar ratio of the promoter with respect to the catalyst precursor is between 1000:1 and 1:1, preferably between 10:1 and 1:1. The amount of catalyst in the reaction mixture calculated on ppm level of the metal in the total mass of the mixture is 1-10,000 ppm, 10-5000 ppm, even 20-2000 ppm. For an in-situ activation, a nitrogen atmosphere is particularly suitable.

The silylhydride employed in the hydrosilylation reaction is not particularly limited. It can be any compound selected from the group consisting of $R^{10}_aSiH_{4-a}$, $(R^{10}O)_aSiH_{4-a}$, $Q_uT_vT_p^HD_wD^H_xM^H_yM_z$, and combinations of two or more thereof. The silylhydride can contain linear, branched or cyclic structures, or combinations thereof. As used herein, each occurrence of $R^{10}$ is independently C1-C18, preferably C1-C10, more preferably C1-C6 alkyl, C1-C18, preferably C1-C10, more preferably C1-C6 substituted alkyl, wherein $R^{10}$ optionally contains at least one heteroatom, each occurrence of a independently has a value from 1 to 3, each of p, u, v, y and z independently has a value from 0 to 20, w and x are from 0 to 1000, provided that p+x+y equals 1 to 3000 and the valences of the all the elements in the silylhydride are satisfied. Preferably, p, u, v, y, and z are from 0 to 10, w and x are from 0 to 100, wherein p+x+y equals 1 to 100.

As used herein, an "M" group represents a monofunctional group of formula $R^{11}_3SiO_{1/2}$, a "D" group represents a difunctional group of formula $R^{11}_2SiO_{2/2}$, a "T" group represents a trifunctional group of formula $R^{11}SiO_{3/2}$, and a "Q" group represents a tetrafunctional group of formula $SiO_{4/2}$, an "$M^H$" group represents $HR^{11}_2SiO_{1/2}$, a "$T^H$" represents $HSiO_{3/2}$, and a "$D^H$" group represents $R^{11}HSiO_{2/2}$. Each occurrence of $R^{11}$ is independently C1-C18, preferably C1-C10, more preferably C1-C6 alkyl, C1-C18, preferably C1-C10, more preferably C1-C6 substituted alkyl, wherein $R^{11}$ optionally contains at least one heteroatom.

The activating silylhydride can, in embodiments, be chosen from a primary silane, a tertiary silane, or combinations thereof. Examples of compounds that are particularly suitable as activating silylhydrides include, but are not limited to, $PhSiH_3$, octylsilane, triethoxysilane, etc.

In one embodiment, the substrate silylhydride is also the activating silylhydride for the purpose of the reaction. In embodiments where the substrates silylhydride is also the activating silylhydride, the process does not require separate additions of that material to the system. For example, it is sufficient to provide that substrate/activating silylhydride to a particular mixture to carry out the process.

The compound containing an unsaturated group employed in the hydrosilylation reaction includes, but is not limited to, unsaturated polyethers such as alkyl-capped allyl polyethers, vinyl functionalized alkyl capped allyl or methallyl polyether; terminally unsaturated amines; alkynes; C2-C18 olefins, preferably alpha olefins; internal olefins; unsaturated cycloalkyl epoxide such as vinyl cyclohexyl epoxide; terminally unsaturated acrylates or methyl acrylates; unsaturated aryl ethers; unsaturated aromatic hydrocarbons; unsaturated cycloalkanes such as trivinyl cyclohexane; unsaturated esters and acids; vinyl-functionalized polymer or oligomer; alkenyl-functional silanes, an alkenyl-functional silicones, and vinyl-functionalized silanes and vinyl-functionalized silicones.

Unsaturated polyethers suitable for the hydrosilylation reaction preferably are polyoxyalkylenes having the general formula:

$R^{12}(OCH_2CH_2)_z(OCH_2CHR^{14})_w—OR^{13}$ (Formula III) or $R^{13}O(CHR^{14}CH_2O)_w(CH_2CH_2O)_z—CR^{15}_2—C≡C—C^{15}_2—(OCH_2CH_2)_z(OCH_2CHR^{14})_wR^{16}$ (Formula IV) or $H_2C=CR^{15}CH_2O(CH_2CH_2O)_z(CH_2CHR^{14}O)_w CH_2CR^{15}=CH_2$ (Formula V)

wherein $R^{12}$ denotes an unsaturated organic group containing from 2 to 10 carbon atoms such as allyl, methallyl, propargyl or 3-pentynyl. When the unsaturation is olefinic, it is desirably terminal to facilitate smooth hydrosilylation. However, when the unsaturation is a triple bond, it may be internal. $R^{13}$ is vinyl, or a polyether capping group of from 1 to 8 carbon atoms such as the alkyl groups: $CH_3$, n-$C_4H_9$, t-$C_4H_9$ or i-$C_8H_{17}$, the acyl groups such as $CH_3COO$, t-$C_4H_9COO$, the beta-ketoester group such as $CH_3C(O)CH_2C(O)O$, or a trialkylsilyl group. $R^{14}$ and $R^{15}$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl groups, for example, benzyl, phenylethyl and nonylphenyl, or the cycloalkyl groups, for example, cyclohexyl and cyclooctyl. $R^{15}$ may also be hydrogen. Methyl is the most preferred $R^{14}$ and $R^{15}$ groups. $R^{16}$ is vinyl, or a polyether capping group of from 1 to 8 carbon atoms as defined herein above for $R^{13}$. Each occurrence of z is 0 to 100 inclusive and each occurrence of w is 0 to 100 inclusive. Preferred values of z and w are 1 to 50 inclusive.

The metal complexes of the invention can also be used in a process for preparing a silylated polyurethane, which includes the step of contacting a terminally unsaturated polyurethane polymer with a silylhydride in the presence of an in-situ activated complex of Formula (I) or (II).

After being activated by the activating silylhydride and promoter, the species formed from Formula I and II are efficient and selective in catalyzing hydrosilylation reactions. For example, when the metal complexes of the invention are employed in the hydrosilylation of an alkyl-capped allyl polyether the reaction products are essentially free of unreacted alkyl-capped allyl polyether and its isomerization products. In one embodiment, the reaction products do not contain the unreacted alkyl-capped allyl polyether and its isomerization products.

Accordingly, in some embodiments, the present invention is also directed to the compositions produced from the above described methods. These compositions contain the hydrosilylated products of the silylhydride and the compound having at least one unsaturated group plus derivatives from the activating agents. The hydrosilylated products that are produced by the process of the present invention have uses in the synthesis of silicone materials such as silanes, adhesives, products for agricultural and personal care applications, and silicone surfactant for stabilizing polyurethane foams.

The following examples are intended to illustrate, but in no way limit the scope of the present invention. All parts and percentages are by weight and all temperatures are in degrees Celsius unless explicitly stated otherwise. All patents, other publications, and U.S. patent applications referred to in the instant application are incorporated herein by reference in their entireties.

EXAMPLES

General Considerations

All air and moisture-sensitive manipulations were carried out using a standard vacuum line, Schlenk, and cannula techniques or in an inert atmosphere drybox containing an atmosphere of purified nitrogen. Methoxypolyethyleneglycolallylether substrate having an average molecular weight of 450 was obtained from NOF Corporation, and sold under the trade name UNIOX PKA5008. All other material was purchased from Aldrich. Solvents and substrates for air and moisture-sensitive manipulations were initially dried and deoxygenated before use. The preparation of PDIFeCl$_2$ complexes is known to people skilled in the art. The $^1$H, $^{13}$C and $^{29}$Si NMR spectra were recorded on a Bruker 200 mHZ and 400 mHz spectrometers. GC analysis was performed using a Aligent 7890A gas chromatograph.

The following abbreviations and terms are used: GC, Gas Chromatography; MS, Mass Spectroscopy; THF, tetrahydrofuran; NMR, Nuclear Magnetic Resonance.

Example 1

Hydrosilylation of 1-Octene with Phenylsilane (PhSiH$_3$) Using $^{Mes}$PDIFeCl$_2$ as a Catalyst Precursor A vial was charged with $^{Mes}$PDIFeCl$_2$ (0.006 g, 0.010 mmol) and purged with nitrogen. A stock solution of $^{Mes}$PDI in THF (1 mL, 29 mM, 0.03 mmol), PhSiH$_3$ (0.4 mL, 0.0032 mol) and octene (0.5 mL, 0.0032 mol) were added to the vial. The reaction was stirred at room temperature for 20 hr. The material was exposed to air, filtered and submitted for analysis. In a first control example, a reaction was performed similarly to the above, except 1 mL of THF was added instead of the $^{Mes}$PDI stock solution. In a second control example, a reaction was performed similarly to the above, except without the addition of the $^{Mes}$PDIFeCl$_2$. The results of these examples are shown in Table 1.

TABLE 1

Hydrosilylation of 1-Octene with Phenylsilane (PhSiH$_3$) using $^{Mes}$PDIFeCl$_2$ as a Catalyst Precursor

| Additives | % Yield* |
|---|---|
| $^{Mes}$PDIFeCl$_2$/$^{Mes}$PDI solution | 40 |
| $^{Mes}$PDIFeCl$_2$ | 21 |
| $^{Mes}$PDI | 0 |

*Yield of PhSioctylH$_2$ was determined by $^{29}$Si NMR.

Example 2

Hydrosilylation of 1-Octene with Phenylsilane (PhSiH$_3$) Using Iron Stearate as a Catalyst Precursor A vial was charged with iron (II) stearate (0.002 g, 0.003 mmol). In a nitrogen filled glovebox, a stock solution of $^{Mes}$PDI in THF (1 mL, 9.6 mM, 0.01 mmol), PhSiH$_3$ (0.4 mL, 0.0032 mol) and octene (0.5 mL, 0.0032 mol) were added to the vial. The reaction was heated to 60° C. for 1 h. The material was exposed to air, filtered and submitted for analysis. In a first control example, a reaction similar to the above was performed, except 1 mL of THF was added instead of the $^{Mes}$PDI stock solution. In a second control example, a reaction similar to above was performed except without the addition of the iron stearate. The results of these examples are shown in Table 2.

TABLE 2

Hydrosilylation of 1-Octene with Phenylsilane (PhSiH$_3$) using Iron Stearate as a Catalyst Precursor

| Additives | % Yield* |
|---|---|
| Iron (II) stearate/MesPDI | 97 |
| Iron (II) stearate | 15 |
| $^{Mes}$PDI | 0 |

*Yield of PhSioctylH$_2$ was determined by $^{29}$Si NMR.

Examples 3-19

Hydrosilylation of 1-Octene with Phenylsilane (PhSiH$_3$) Using a Metal Salt as a Catalyst Precursor and $^{Mes}$PDI as a Promoter In a nitrogen filled glovebox, a vial was charged with the metal salt (0.011 mmol). A stock solution of $^{Mes}$PDI in THF (1 mL, 35 mM, 0.035 mmol), PhSiH$_3$ (0.4 mL, 0.0032 mol) and octene (0.5 mL, 0.0032 mol) were added to the vial. The reaction was heated to 60° C. for 5 h. The material was exposed to air, filtered and submitted for analysis. The results are shown in Table 3.

TABLE 3

Hydrosilylation of 1-Octene with Phenylsilane (PhSiH$_3$) with Metal Salts as a Catalyst Precursor and $^{Mes}$PDI as a Promoter

| Example | Metal salt | % Yield* |
|---|---|---|
| 3 | Iron (II) stearate | 95 |
| 4 | Iron (II) acetate | 75 |
| 5 | Iron (II) chloride | 43 |
| 6 | Iron (II) triflate | 11 |
| 7 | Iron (III) acetylacetonate | 41 |
| 8 | Iron (III) citrate | 25 |
| 9 | Hematite | 22 |
| 10 | Magnetite | 7 |
| 11 | Ruthenium chloride | 7 |
| 12 | Manganese (III) acetylacetonate | 51 |
| 13 | Iron (II) oxalate | 0 |
| 14 | Iron (III) tartrate | 0 |
| 15 | Copper (I) chloride | 0 |
| 16 | Copper (II) chloride | 0 |
| 17 | Copper (II) acetate | 0 |
| 18 | Zinc (II) chloride | 0 |
| 19 | Zinc (II) acetate | 0 |

*Yield of PhSioctylH$_2$ was determined by $^{29}$Si NMR.

Example 20

Hydrosilylation of Octene with Phenylsilane (PhSiH$_3$) Using a Metal Salt as a Catalyst Precursor and $^{Mes}$PDI as a Promoter Experiments with metal salts were run similar to what is described in Example 3. The reactions were run with either 1-octene or 2-octene as the unsaturated substrate as indicated in the table below. The ratio of the terminal and internal addition products (Products A and B) from the hydrosilylation was determined. The results are shown in Table 4.

TABLE 4

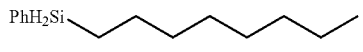

Hydrosilylation of Octene with Phenylsilane (PhSiH₃) using a Metal Salt as a Catalyst Precursor and $^{Mes}$PDI as a promoter

| Metal salt | olefin | % Yield Product A | % Yield Product B |
|---|---|---|---|
| Manganese (III) acetylacetonate | 1-octene | 51 | 0 |
| Iron (II) stearate (Ex.3) | 1-octene | 95 | 3 |
| Cobalt (II) stearate | 1-octene | 0 | 100 |
| Cobalt (III) acetylacetonate | 1-octene | 0 | 100 |
| Nickel (II) stearate | 1-octene | 23 | 41 |
| Nickel (II) acetylacetonate | 1-octene | 50 | 50 |
| Cobalt (II) chloride | 1-octene | 0 | 100 |
| Iron (II) stearate | 2-octene | 0 | >98 |

Examples 21-24

Hydrosilylation of 1-Octene with Phenylsilane (PhSiH₃), with Iron Stearate Used as a Catalyst Precursor and $^R$PDI as Promoter The examples below were run in a similar manner except that the reactions were run with 1 mL THF, 1 mL toluene, or neat as indicated in the table below. A vial was charged with the iron (II) stearate (0.004 g, 0.006 mmol) and the PDI additive (0.019 mmol). In a nitrogen filled glovebox, the vial was charged with toluene (1 mL), PhSiH₃ (0.4 mL, 0.0032 mol) and octene (0.5 mL, 0.0032 mol). The reaction was heated to 80° C. Aliquots of the reaction mixture were taken periodically and tested by GC. After the reaction was judged complete by GC, the material was exposed to air, filtered and submitted for analysis. The results are shown in Table 5.

TABLE 5

Hydrosilylation of 1-Octene with Phenylsilane (PhSiH₃), with Iron Stearate used as a Catalyst Precursor and $^R$PDI as Promoter

| Example | Additive | % Yield* | Time (h) |
|---|---|---|---|
| 21 | $^{Mes}$PDI | 94 | 1 |
| 22 | $^{Ph}$PDI | 93 | 1 |
| 23 | $^{Et2}$PDI | 100 | 5 |
| 24 | $^{iPr2}$PDI | 87 | 9 |

*Yield of PhSioctylH₂ was determined by Si NMR.
($^{Ph}$PDI = (2-C₆H₅—C₆H₂N=CMe)₂C₅H₃N, $^{Et2}$PDI = (2,6-Et₂—C₆H₂N=CMe)₂C₅H₃N, $^{iPr2}$PDI = 2,6-$^i$Pr₂—C₆H₂N=CMe)₂C₅H₃N)

Examples 25-34

Hydrosilylation of 1-Octene with an Silylhydride, with Iron Stearate Used as a Catalyst Precursor and a $^{Mes}$PDI Promoter A vial was charged with the iron (II) stearate (0.002 g, 0.003 mmol). In a nitrogen filled glovebox, the vial was charged with a stock solution of $^{Mes}$PDI in THF (1 mL, 10 mM, 0.010 mmol), silylhydride (0.032 mol), octene (0.5 mL, 0.032 mol). The reaction was heated to 60° C. for 5 h. The results are shown in Table 6. All examples were run similarly except that the reactions were run with 1 mL THF, 1 mL toluene, or neat as indicated in the table below.

TABLE 6

Hydrosilylation of 1-Octene with an Organosilane, with Iron Stearate used as a Catalyst Precursor and a PDI Promoter

| Example | Silane | Solvent | % Yield* |
|---|---|---|---|
| 25 | PhSiH₃ | THF | 97% |
| 26 | PhSiH₃ | toluene | 95% |
| 27 | PhSiH₃ | neat | 92% |
| 28 | OctylSiH₃ | THF | 50% |
| 29 | OctylSiH3 | toluene | 0% |
| 30 | Me(EtO)₂SiH | THF | 53% |
| 31 | Me(EtO)₂SiH | toluene | 3% |
| 32 | Me(EtO)₂SiH | neat | 61% |
| 33 | Si(OEt)₃H | toluene | 25% |
| 34 | Si(OEt)₃H | neat | 27% |

*% Yield is given for the mono-hydrosilylated product determined by ²⁹Si NMR

Examples 35-74

Hydrosilylation of 1-Octene with Phenylsilane (PhSiH₃) Using Iron Stearate as a Catalyst Precursor and Various Promoters A vial was charged with iron (II) stearate (0.004 g, 0.006 mmol) and an additive (0.018 mmol). In a nitrogen filled glovebox THF (2 mL), PhSiH₃ (0.8 mL, 0.0064 mol) and octene (1.0 mL, 0.0064 mol) were added to the vial. The reaction was heated to 60° C. for 5 h. The material was exposed to air, filtered and submitted for analysis.

| Example | Additive | % Yield |
|---|---|---|
| 35 | $^{Mes}$PDI | >95 |
| 36 | $^{ipr2}$Impy | 11 |
| 37 | R-$^{ipr2}$pybox | 22 |
| 38 | salen | 22 |
| 39 | 2,6-diacetylpyridine | 56 |
| 40 | 2,6-dimethanolpyridine | 51 |
| 41 | 2,6-dicarboxyamidepyridine | 34 |
| 42 | 2-acetylpyridine | 27 |
| 43 | 2-acetylphenol | 31 |
| 44 | TMEDA | 21 |
| 45 | proton sponge | 20 |
| 46 | triethanolamine | 32 |
| 47 | pinacol | 30 |
| 48 | catechol | 0 |
| 49 | 2-aminophenol | 20 |
| 50 | 2-hydroxypyridine | 15 |
| 51 | proline | 0 |
| 52 | bpy | 5 |
| 53 | tpy | 0 |
| 54 | $^t$Bu₃-tpy | 1 |
| 55 | potassium tris(pyrazolyl)borate | 0 |
| 56 | tris(pyrazolyl)methane | 28 |
| 57 | imidazole | 22 |
| 58 | N-methyl imidazole | 14 |
| 59 | benzimidazole | 24 |
| 60 | OEP | 0 |
| 61 | TPP | 2 |
| 62 | phthalcyanine | 11 |
| 63 | sodium formate | 32 |
| 64 | sodium acetate | 24 |
| 65 | sodium stearate | 20 |
| 66 | sodium benzoate | 31 |
| 67 | lithium acetylacetonate | 30 |
| 68 | sodium citrate tribasic | 29 |
| 69 | citric acid | 0 |
| 70 | TBAF | 18 |
| 71 | PCy₃ | 21 |
| 72 | BINAP | 25 |

-continued

| Example | Additive | % Yield |
|---------|----------|---------|

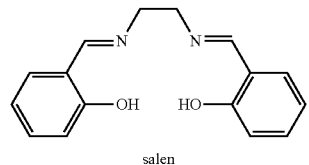 [SMILES: Oc1ccccc1/C=N/CC/N=C/c1ccccc1O]
salen

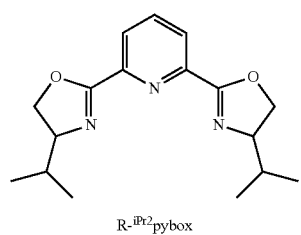 [SMILES: CC(C)C1COC(c2cccc(C3=NC(C(C)C)CO3)n2)=N1]
R-$^{iPr2}$pybox

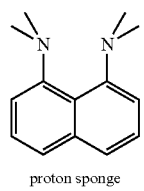 [SMILES: CN(C)c1cccc2cccc(N(C)C)c12]
proton sponge

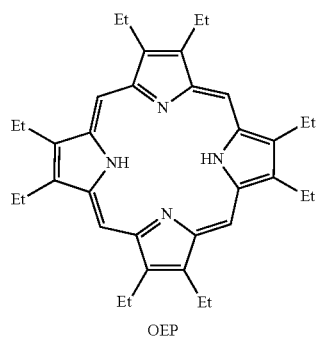 [SMILES: CCC1=C(CC)c2cc3[nH]c(cc4nc(cc5[nH]c(cc1n2)c(CC)c5CC)C(CC)=C4CC)c(CC)c3CC]
OEP

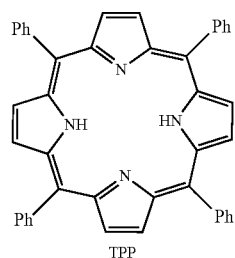
TPP

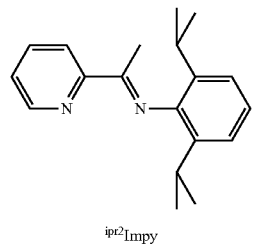 [SMILES: C/C(=N\c1c(C(C)C)cccc1C(C)C)c1ccccn1]
$^{ipr2}$Impy

Example 73

Hydrosilylation of 1-Octene with Methylbis(Trimethylsiloxy)Silane (MD$^H$M), with PhSiH$_3$ Used as a Activating Silylhydride, Iron Stearate as a Catalyst Precursor and $^{Mes}$PDI as a Promoter A vial was charged with the iron (II) stearate (0.008 g, 0.013 mmol) and the $^{Mes}$PDI additive (0.0153 g, 0.039 mmol). In a nitrogen filled glovebox, the vial was charged with THF (1 mL) and PhSiH$_3$ (0.25 mL, 0.002 mol). The reaction was heated to 60° C. for 1 h to afford a brown solution. A second vial was charged with octene (0.5 mL, 0.0032 mol) and MD$^H$M (0.86 mL, 0.0032 mol). To the second vial, 0.25 mL of the brown solution was added. The material was heated to 60° C. for an additional hour. The material was exposed to air, filtered and submitted for analysis. The product was recovered in >80% yield.

Example 74

Hydrosilylation of 1-Octene with Triethoxysilane, with PhSiH$_3$ Used as a Activating Silylhydride, Iron Stearate as a Catalyst Precursor and $^{Mes}$PDI as a Promoter A vial was charged with the iron (II) stearate (0.008 g, 0.013 mmol) and the $^{Mes}$PDI additive (0.0153 g, 0.039 mmol). In a nitrogen filled glovebox, the vial was charged with THF (1 mL) and PhSiH$_3$ (0.25 mL, 0.002 mol). The reaction was heated to 60° C. for 1 h to afford a brown solution. A second vial was charged with octene (0.5 mL, 0.0032 mol) and Si(OEt)$_3$H (0.59 mL, 0.0032 mol). To the second vial, 0.25 mL of the brown solution was added. The material was heated to 60 C for an additional hour. The material was exposed to air, filtered and submitted for analysis. The octylSi(OEt)$_3$ product was recovered in >90% yield.

Example 75

Hydrosilylation of Methyl-Capped Allyl Polyether with MD$^H$M, with PhSiH$_3$ Used as an Activator and Iron Stearate as a Catalyst Precursor and $^{Mes}$PDI Used as a Promoter A vial was charged with the iron (II) stearate (0.015 g, 0.024 mmol) and the $^{Mes}$PDI additive (0.029 g, 0.072 mmol). In a nitrogen filled glovebox, the vial was charged with THF (1 mL) and PhSiH$_3$ (0.25 mL, 0.002 mol). The reaction was heated to 60° C. for 1 h to afford a brown solution. A second vial was charged with methyl-capped allyl polyether substrate (PKA5008, 0.0032 mol) and MD$^H$M (0.0032 mol). To the second vial, 0.25 mL of the brown solution was added. The material was heated to 60 C for an additional 5 hour. The material was exposed to air, filtered and submitted for analysis. The product was recovered in >40% yield.

What is claimed is:
1. A process for the hydrosilylation of an unsaturated compound comprising at least one carbon-carbon unsaturated group with a silylhydride in the presence of a metal complex of Formula (I), Formula (II), or a combination thereof:

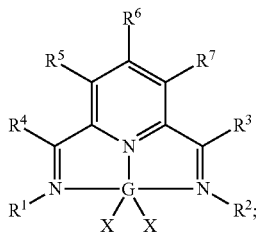

Formula (I)

GXn Formula (II);

wherein the process comprises activating the metal complex with a silylhydride and a promoter compound, and G is Mn, Fe, Ni, Ru, or Co; each occurrence of $R^1$, $R^2$, $R^3$, $R^4$, $R^5$, $R^6$, $R^7$, is independently H, C1-18 alkyl, C1-C18 substituted alkyl, aryl, substituted aryl, or an inert group, wherein any two neighboring $R^1$, $R^2$, $R^3$, $R^4$, $R^5$, $R^6$, and $R^7$ groups taken together may form a ring being a substituted or unsubstituted, saturated, or unsaturated cyclic structure, wherein $R^1$-$R^7$ other than hydrogen, optionally contain at least one heteroatom; X in Formula (I) is an anion;

X in Formula (II) is an anion or an oxygen atom, and n=1-3 including non-integers, and wherein the promoter compound is an organic compound that is other than a reducing agent.

2. The process of claim 1, wherein a single silylhydride is employed for activating the metal complex and for the hydrosilylation reaction.

3. The process of claim 2, wherein the silylhydride is chosen from phenylsilane.

4. The process of claim 2, wherein the silylhydride is triethoxysilane.

5. The process of claim 1, wherein the silylhydride employed to activate the metal complex is different than the silylhydride undergoing hydrosilylation with the unsaturated compound.

6. The process of claim 5, wherein the silylhydride employed to activate the metal complex is chosen from phenylsilane and triethoxysilane, and the silylhydride undergoing hydrosilylating the unsaturated compound is chosen from $R^{10}{}_a SiH_{4-a}$, $(RO)_a SiH_{4-a}$, $Q_u T_v T_p{}^H D_w D^H{}_x M^H{}_y M_z$, and combinations thereof, wherein Q is $SiO_{4/2}$, T is $R^4 SiO_{3/2}$, $T^H$ is $HSiO_{3/2}$, D is $R^{11}{}_2 SiO_{2/2}$, $D^H$ is $R^{11} HSiO_{2/2}$, $M^H$ is $HR^{11}{}_2 SiO_{1/2}$, M is $R'_3 SiO_{1/2}$, each occurrence of R and R' is independently C1-C18 alkyl, C1-C18 substituted alkyl, wherein $R^{10}$ and $R^{11}$ optionally contain at least one heteroatom, each occurrence of a independently has a value from 1 to 3, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of the all the elements in the silylhydride are satisfied.

7. The process of claim 1 wherein the promoter has a pKb greater than 9.7.

8. The process of claim 1 wherein the promoter is selected from the group consisting of pyridine(di)imine type compounds, 2,6-dimethanolpyridine, 2,6-diacetylpyridine, tetramethylethylenediamine (TMEDA), tetrabutylammonium fluoride (TBAF), NaOAc, Liacac, and N and O containing ligands, or combinations of two or more thereof.

9. The process of claim 1 wherein the promoter is $^{Mes}$PDI (($2,4,6Me_3C_6H_2N=CMe)_2(C_5H_3N$)).

10. The process of claim 1, wherein Formula (I) is $^{Mes}$PDIFeCl$_2$ (($2,4,6Me_3 C_6H_2N=CMe)_2(C_5H_3N)FeCl_2$).

11. The process of claim 1, wherein X in Formula (I) or Formula (II) is chosen from F$^-$, Cl$^-$, Br$^-$, I$^-$, an enolate, an acetylacetonate, $CF_3R^8SO_3{}^-$ or $R^9COO^-$, wherein $R^8$ is a covalent bond or a C1-C6 alkylene group, and $R^9$ is a C1-C10 substituted or unsubstituted hydrocarbyl group, optionally containing at least one heteroatom.

12. The process of claim 1, wherein the unsaturated organic substrate contains an internal olefin.

13. The process of claim 12, wherein said process produces an internal addition product.

14. The process of claim 13, wherein said internal addition product is converted into an internal alcohol.

15. The process of claim 1, wherein said process produces an internal addition product.

16. The process of claim 15, wherein said internal addition product is converted into an internal alcohol.

17. The process of claim 1, wherein the complex according to Formula (I) is immobilized on a support.

18. The process of claim 17, wherein the support is selected from the group consisting of carbon, silica, alumina, MgCl$_2$, zirconia, polyethylene, polypropylene, polystyrene, poly(aminostyrene), dendrimers, and combinations thereof.

19. The process of claim 18, wherein at least one of $R^1$-$R^7$ contains a functional group that covalently bonds with the support.

20. The process of claim 1, wherein the silylhydride for hydrosilylating the unsaturated compound is selected from the group consisting of $R^{10}{}_a SiH_{4-a}$, $(RO)_a SiH_{4-a}$, $Q_u T_v T_p{}^H D_w D^H{}_x M^H{}_y M_z$, and combinations of two or more thereof, wherein Q is $SiO_{4/2}$, T is $R^4 SiO_{3/2}$, $T^H$ is $HSiO_{3/2}$, D is $R^{11}{}_2 SiO_{2/2}$, $D^H$ is $R^{11} HSiO_{2/2}$, $M^H$ is $HR^{11}{}_2 SiO_{1/2}$, M is $R'_3 SiO_{1/2}$, each occurrence of R and R' is independently C1-C18 alkyl, C1-C18 substituted alkyl, wherein $R^{10}$ and $R^{11}$ optionally contain at least one heteroatom, each occurrence of a independently has a value from 1 to 3, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of the all the elements in the silylhydride are satisfied.

21. The process of claim 20, wherein p, u, v, y, and z are from 0 to 10, w and x are from 0 to 100, wherein p+x+y equals 1 to 100.

22. The process of claim 1, wherein the compound containing an unsaturated group is selected from the group consisting of an alkyl-capped allyl polyether, a vinyl functionalized alkyl-capped allyl or methallyl polyether, a terminally unsaturated amine, an alkyne, a C2-C40 olefin, an unsaturated alkyl or cycloalkyl epoxide, a terminally unsaturated acrylate or methyl acrylate, an unsaturated aryl ether, an aralkene or aralkyne, an unsaturated cycloalkane, an internal olefin, an unsaturated acid or ester, a vinyl-functionalized polymer or oligomer, an alkenyl-functional silane, an alkenyl-functional silicone, a vinyl-functionalized silane, a vinyl-functionalized silicone, and combinations thereof.

23. The process of claim 1, wherein the compound containing an unsaturated group is a polyoxyalkylene having the generic formula:

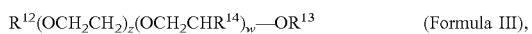

(Formula III),

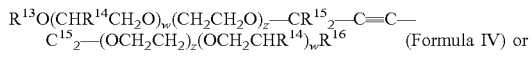

(Formula IV) or

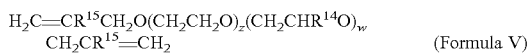

(Formula V)

wherein each occurrence of $R^{12}$ is an unsaturated organic group containing from 2 to 10 carbon atoms, each occurrence of $R^{13}$ is independently hydrogen, vinyl, or a polyether capping group of from 1 to 8 carbon atoms, each occurrence of $R^{14}$ and $R^{15}$ are independently monovalent hydrocarbon groups, except that $R^{15}$ can also be chosen from hydrogen each occurrence of $R^{16}$ is vinyl, or a polyether capping group of from 1 to 8 carbon atoms, each occurrence of z is 0 to 100 inclusive, and each occurrence of w is 0 to 100 inclusive.

24. The process of claim 1 wherein the reaction is carried out at a temperature of −40 C to 200 C.

25. The process of claim 1 wherein the reaction is conducted under an inert atmosphere.

26. The process of claim 1 wherein the reaction is conducted neat or in the presence of a solvent selected from the group consisting of hydrocarbons, halogenated hydrocarbons, ethers, and combination thereof.

27. The process of claim 1, wherein Formula (II) is iron stearate.

28. The process of claim 1, wherein Formula (II) is an iron oxide.

29. The process of claim 1 further comprising removing the complex and or derivatives thereof from the hydrosilylated product.

30. A composition produced by a process according to claim 1, wherein the composition contains the catalyst and/or derivatives thereof.

31. A composition produced by the process of claim 1, wherein the compound containing an unsaturated group is an alkyl-capped allyl polyether; and wherein the composition is essentially free of unreacted alkyl-capped allyl polyether and its isomerization products.

32. A composition produced by the process of claim 1, wherein the compound containing at least one unsaturated group is a vinyl-functionalized silicone.

33. The process of claim 1, wherein the silylhydride, unsaturated compound, promoter, and metal complex are provided in one solution.

34. The process of claim 1 comprising adding a solution comprising the silylhydride, the unsaturated compound, and the promoter to a solution comprising the metal complex.

35. The process of claim 1 comprising (a) providing a solution comprising the metal complex and the promoter, and (b) adding a solution comprising the silylhydride and the unsaturated compound to the solution of (a).

36. A process for the hydrosilylation of a composition containing a silylhydride and a compound containing at least one unsaturated group, the process comprising:
    reacting a substrate silylhydride with a compound containing at least one carbon-carbon unsaturated group in the presence of an activating silylhydride, a promoter compound, and a metal complex to produce a hydrosilylation product containing said complex and/or derivatives thereof,
    wherein the metal complex is chosen from a complex of Formula (I), Formula (II), or a combination thereof; where Formula (I) is:

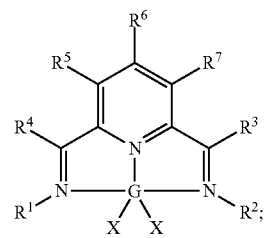

Formula (II) is: $GX_n$; G is Mn, Fe, Ni, Ru, or Co; each occurrence of $R^1$, $R^2$, $R^3$, $R^4$, $R^5$, $R^6$, $R^7$, is independently H, C1-18 alkyl, C1-C18 substituted alkyl, aryl, substituted aryl, or an inert form a ring being a substituted or unsubstituted, saturated, or unsaturated cyclic structure, wherein $R^1$-$R^7$ other than hydrogen, optionally contain at least one heteroatom; X in Formula (I) is an anion; X in Formula (II) is an anion or an oxygen atom, and n=1-3 including non-integers, and wherein the promoter compound is an organic compound that is other than a reducing agent.

37. The process of claim 36, wherein the substrate silylhydride is also the activating silylhydride and can be added as a single material.

38. The process of claim 37, wherein the substrate silylhydride is phenylsilane.

39. The process of claim 37, wherein the substrate silylhydride is triethoxysilane.

40. The process of claim 36, wherein substrate silylhydride is different from the activating silylhydride.

41. The process of claim 36, wherein the activating silylhydride is phenylsilane.

42. The process of claim 36, wherein the activating silylhydride is triethoxysilane.

43. The process of claim 36, wherein the reacting step comprises (a) providing a mixture of the metal complex, the promoter, and the activating silylhydride, (b) providing a mixture of the substrate silylhydride and the unsaturated compound, and adding (b) to (a).

44. The process of claim 36, wherein the reacting step comprises (a) providing a mixture of the metal complex, the unsaturated compound, the promoter, and the activating silylhydride, (b) providing a composition comprising the substrate silylhydride, and adding (b) to (a).

45. The process of claim 36, wherein the reacting step comprises (a) providing a mixture of the metal complex, the substrate silylhydride, the promoter, and the activating silylhydride, (b) providing a composition comprising the unsaturated compound, and adding (b) to (a).

46. The process of claim 1 having a molar ratio of the promoter to the metal complex of from 1000:1 to 1:1.

47. The process of claim 1 having a molar ratio of the promoter to the metal complex of from 10:1 to 1:1.

48. The process of claim 36 having a molar ratio of the promoter to the metal complex of from 1000:1 to 1:1.

49. The process of claim 36 having a molar ratio of the promoter to the metal complex of from 10:1 to 1:1.

* * * * *